United States Patent
Silverstrini

(10) Patent No.: US 6,214,044 B1
(45) Date of Patent: *Apr. 10, 2001

(54) HYBRID INTRASTROMAL CORNEAL RING

(75) Inventor: Thomas A. Silverstrini, Alamo, CA (US)

(73) Assignee: KeraVision, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/467,618

(22) Filed: Jun. 6, 1995

Related U.S. Application Data

(62) Division of application No. 07/927,165, filed on Aug. 7, 1992, now abandoned.

(51) Int. Cl.$^7$ ........................................................ A61F 2/14
(52) U.S. Cl. ........................................ 623/5.12; 623/5.16
(58) Field of Search ................................ 623/5; 606/107, 606/166, 167

(56) References Cited

U.S. PATENT DOCUMENTS

| | | |
|---|---|---|
| 4,316,292 | 2/1982 | Alexeev . |
| 4,439,196 | 3/1984 | Higuchi . |
| 4,452,235 | 6/1984 | Reynolds ................................ 623/5 |
| 4,455,143 | 6/1984 | Theeuwes et al. . |
| 4,624,669 * | 11/1986 | Grendahl ................................ 623/5 |
| 4,647,282 | 3/1987 | Federov et al. ........................ 623/4 |
| 4,671,276 | 6/1987 | Reynolds . |
| 4,688,570 | 8/1987 | Kramer et al. . |

(List continued on next page.)

FOREIGN PATENT DOCUMENTS

| | | |
|---|---|---|
| 0420549 | 4/1991 | (EP) . |
| 2608041 | 6/1988 | (FR) . |
| 2095119 | 12/1981 | (GB) . |
| 89/04153 * | 5/1989 | (WO) ....................................... 623/5 |
| WO 92/00112 | 1/1992 | (WO) . |

OTHER PUBLICATIONS

Temirov et al., "Refractive circular tunnel keroplasty in the correction of high myopia" *Vestnki Oftalmologii* (1991) 3:23–31.

Simón et al., "Refractive remodelling of the cornea by intrastromal rings" *Abstracts: Eighth International Congress of Eye Research*, Proceedings of the International Society for Eye Research, San Francisco, California, USA, Sep. 4–8, 1988, vol. V, (abstract No. 47).

Simón et al., "Refractive remodelling of the cornea by intrastromal rings" *The Association for Research in Vision and Ophthalmology*, Annual Spring Meeting, Sarasota, Florida, USA, Apr. 30–May 5, 1989, p. 187, (abstract 43).

Blavatskaia, "The use of intralamellar homoplasty in order to reduce refraction of the eye" *Überstzt. Aus. Oftalmol. Zh.* (1966) 7:530–537 which was apparently translated to *Arch. Soc. Ophthalmol.* (1988) 6:311–325. A complete English translation was previously enclosed.

English translation of Brazilian Patent No. BR 8705060 (Mar. 21, 1989).

Hartmann et al., "Intrastromal implantation of an adjustable plastic ring to alter the corneal refraction" delivered by H. Freyler et al., Congress for German Society for Intraocular Lens Implantation, Mar. 1989, pp. 465–475 (English translation enclosed).

*Primary Examiner*—David H. Willse
(74) *Attorney, Agent, or Firm*—Harry J. Macey; KeraVision, Inc.

(57) ABSTRACT

This invention is an intrastromal corneal ring having comprising at least one outer layer of a physiologically compatible polymer having a low modulus of elasticity, which polymer may be hydratable and may be hydrophilic. The inner portion of the hybrid intrastromal corneal ring may be hollow or may contain one or more physiologically compatible polymers.

33 Claims, 4 Drawing Sheets

U.S. PATENT DOCUMENTS

| | | |
|---|---|---|
| 4,693,939 | 9/1987 | Ofstead ..................................... 623/5 |
| 4,709,996 | 12/1987 | Michelson ................................ 623/6 |
| 4,731,080 * | 3/1988 | Galin ........................................ 623/6 |
| 4,766,895 | 8/1988 | Reynolds . |
| 4,799,931 | 1/1989 | Lindstrom ................................ 623/5 |
| 4,815,463 | 3/1989 | Hanna . |
| 4,819,617 | 4/1989 | Goldberg et al. ........................ 623/6 |
| 4,851,003 * | 7/1989 | Lindstrom ................................ 623/5 |
| 4,941,093 | 7/1990 | Marshall et al. ......................... 606/5 |
| 4,961,744 | 10/1990 | Kilmer et al. ........................ 606/166 |
| 4,976,719 | 12/1990 | Siepser ................................. 606/151 |
| 4,983,181 | 1/1991 | Civerchia ................................. 623/5 |
| 5,067,961 | 11/1991 | Kelman et al. .......................... 623/5 |
| 5,090,955 | 2/1992 | Simon .................................. 606/107 |
| 5,098,443 | 3/1992 | Parel et al. ............................... 623/4 |
| 5,300,114 | 4/1994 | Gwon et al. . |
| 5,372,580 | 12/1994 | Simon et al. ......................... 606/107 |
| 5,391,201 | 2/1995 | Barrett et al. . |
| 5,405,384 | 4/1995 | Silvestrini . |

* cited by examiner

HYBRID INTRASTROMAL CORNEAL RING

This application is a division of application Ser. No. 07/927,165, filed Aug. 7, 1992, now abandoned.

FIELD OF THE INVENTION

This invention is a hybrid intrastromal corneal ring ("ICR") comprising at least one outer layer of a physiologically compatible polymer having a low modulus of elasticity, which polymer may be hydratable and may be hydrophilic. The inner portion of the ICR may be hollow or may contain one or more physiologically compatible polymers.

BACKGROUND OF THE INVENTION

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. In contrast, when the front-to-back distance of eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea is aspherical and refracts light in a different meridian at different distances. Some degree of astigmatism is normal, but where it is pronounced, the astigmatism must be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

Another method for correcting those disorders is through the implantation of polymeric rings in the eye's corneal stroma to change the curvature of the cornea. Previous work involving the implantation of polymethylmethacrylate (PMMA) rings, allograft corneal tissue, and hydrogels is well documented. One of the ring devices involves a split ring design which is inserted into a channel previously dissected in the stromal layer of the cornea. A minimally invasive incision is used both for producing the channel and for implanting the implant.

The use of instastromal corneal rings made completely of certain hard, hydrophobic polymers is known. For instance, in the article "Intrastromal Implantation Eines Justierbaren Kunststofforings Zur Hornhautrefraktionsanderung", Hartmann et al., Kongress der Deutschen Gesellschaft fur Intraokularingen Implantation, delivered by h. Fryler et al., Spring-Verlag, Wien, pages 465–475, the use of intrastromal ring implants of rings of silicone, polymethylmethacrylate ("PMMA"), and fluorocarbons TEFLON®, a PTFE available from DuPont. Other disclosures of the use of PMMA in such intrastromal rings is found in U.S. Pat. No. 4,452,235 to Reynolds; U.S. Pat. No. 4,671,276 to Reynolds; U.S. Pat. No. 4,766,895 to Reynolds; and U.S. Pat. No. 4,961,744 to Kilmer et al. These documents do not suggest the use of multiple-layers of differing materials in the intrastromal corneal ring.

The use of soft polymers as intrastromal inserts is not widely known. For instance, U.S. Pat. No. 5,090,955 to Simon, suggests an ICR which is made by introducing a settable polymer into an intrastromal channel which has been previously made and allowing the polymer to set. This procedure does not allow the surgeon to specify the size of the resulting ring nor is it a process which allows control of the flowing polymer within the eye.

Temirov et al, "Refractive circular tunnel keroplasty in the correction of high myopia", Vestnik Oftalmologii 1991: 3-21-31, suggests the use of collagen thread as intrastromal corneal rings material.

They specifically do not suggest the use of soft or hydrophilic polymers insertable into the cornea as intrastromal corneal rings.

SUMMARY OF THE INVENTION

This invention is a hybrid intrastromal corneal ring comprising at least one outer layer of a soft, low modulus, often hydrophilic, physiologically compatible polymer.

The portion of the ICR inside that outer layer may be hollow and adapted to be fillable with a biologic agent, drug or other liquid, emulsified, or time-release eye treatment material. The inner portion may comprise variously a core of a high modulus, physiologically compatible polymer or a further composite of a low modulus polymer or a high modulus polymer core or a high modulus polymer or a low modulus polymer core. The inner portion may comprise a polymeric material which is polymerized in situ after introduction into a hollow center layer.

The term "high modulus polymer" is meant to include physiologically compatible polymers such as PMMA; TEFLON; certain longer chain silicones; polycarbonate; and polyolefins such as polyethylene, polypropylene, polybutylene, their mixtures or other polyolefin interpolymers. The term "low modulus polymer" is meant to include physiologically compatible polymers and hydrogels, such as polyhydroxyethyl methacrylate ("polyHEMA") or polyvinylpyrrolidone ("PVP") or elastomeric materials and biologic polymers such as crosslinked dextran, hyaluronic acid, and heparin or the like. The low modulus hydratable polymers, in any case, may be of the type which is sufficiently cross-linked such that they do not swell upon contact with water (and subsequent hydration) or of the type which swells when hydrated. Additionally, the class of low modulus polymers is meant to include elastomeric polymers, e.g., latex rubber, colloids of polyester and polyether, polyurethanes, lower molecular weight silicones, isoprene, and the like, which are stable and physiologically compatible. Finally, the low modulus polymer may be a reinforced hydrogel such as an interpenetrating network of polymerized vinyl pyrrolidone and methyl methacrylate.

Our intrastromal corneal rings may be implanted into the stroma using a number of known techniques. If hydratable polymers are used, they may be hydrated before or after introduction into the intrastromal passageway created by the surgical device used to introduce these devices into the eye. If the outer layer is hydrated before insertion into the eye, the final size of the ring is set before that insertion. If the hydratable polymers are allowed to hydrate within the corneal space, the device (if appropriate polymers are chosen) will swell within the eye to its final size. If prehydrated, the outer layer often provides a measure of lubricity to the ICR, allowing it to be inserted with greater ease. Other of the noted low modulus polymers may also provide such lubricity.

This invention allows for adjustment of intrastromal corneal rings thickness and diameter and provides a softer interface between a harder polymer core and corneal tissue.

DESCRIPTION OF THE INVENTION

Prior to explaining the details of the inventive devices, a short explanation of the physiology of the eye is needed to appreciate the functional relationship of the intrastromal corneal ring to the eye.

Figure 1:
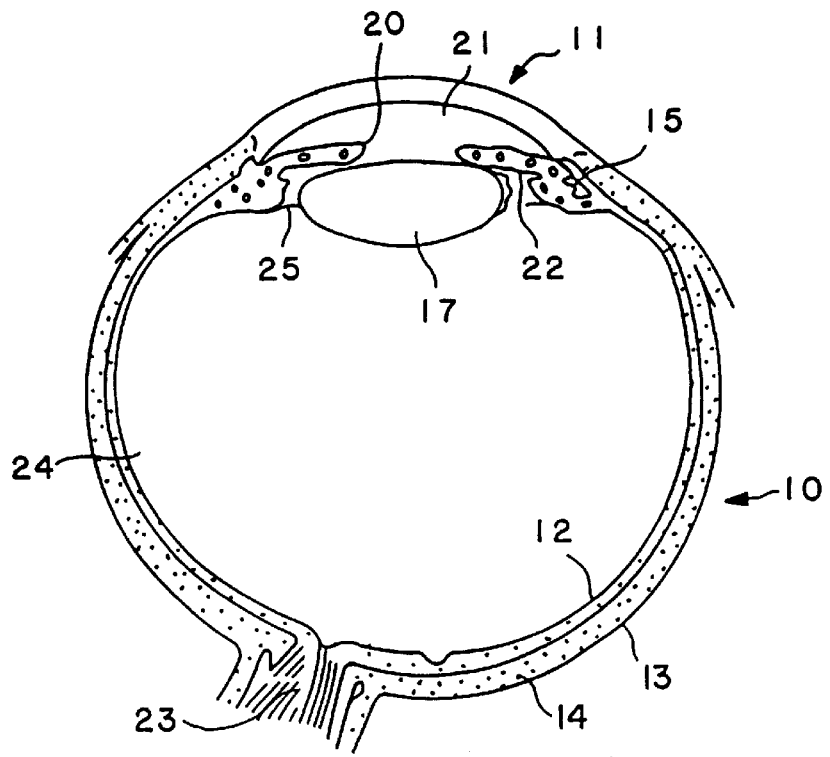
FIG. 1 is a schematic illustration of a horizontal section of the eye.

FIG. 1 shows a horizontal cross-section of the eye with the globe (10) of the eye resembling a sphere with an anterior bulged spherical portion representing the cornea (11).

The globe (10) of the eye consists of three concentric coverings enclosing the various transparent media through which the light must pass before reaching the light-sensitive retina (12). The outermost covering is a fibrous protective portion the posterior five-sixths of which is white and opaque and called the sclera (13), and sometimes referred to as the white of the eye where visible to the front. The anterior one-sixth of this outer layer is the transparent cornea (11).

A middle covering is mainly vascular and nutritive in function and is made up of the choroid (14), ciliary body (15), and iris (16). The choroid generally functions to maintain the retina (12). The ciliary body (15) is involved in suspending the lens (17) and accommodation of the lens. The iris (16) is the most anterior portion of the middle covering of the eye and is arranged in a frontal plane. It is a thin circular disc similar in function to the diaphragm of a camera, and is perforate near its center by a circular aperture called the pupil (20). The size of the pupil varies to regulate the amount of light which reaches the retina (12). It contracts also to accommodation, which serves to sharpen the focus by diminishing spherical aberration. The iris divides the space between the cornea (11) and the lens (17) into an anterior chamber (21) and posterior chamber (22). The innermost portion of covering is the retina (12), consisting of nerve elements which form the true receptive portion for visual impressions.

The retina (12) is a part of the brain arising as an outgrowth from the fore-brain, with the optic nerve (23) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (24) is a transparent gelatinous mass which fills the posterior four-fifths of the globe (10). At its sides it supports the ciliary body (15) and the retina (12). A frontal saucer-shaped depression houses the lens.

The lens (17) of the eye is a transparent bi-convex body of crystalline appearance placed between the iris (16) and vitreous body (24). Its axial diameter varies markedly with accommodation. A ciliary zonule (25), consisting of transparent fibers passing between the ciliary body (15) and lens (17) serves to hold the lens (17) in position and enables the ciliary muscle to act on it.

Referring again to the cornea (11), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
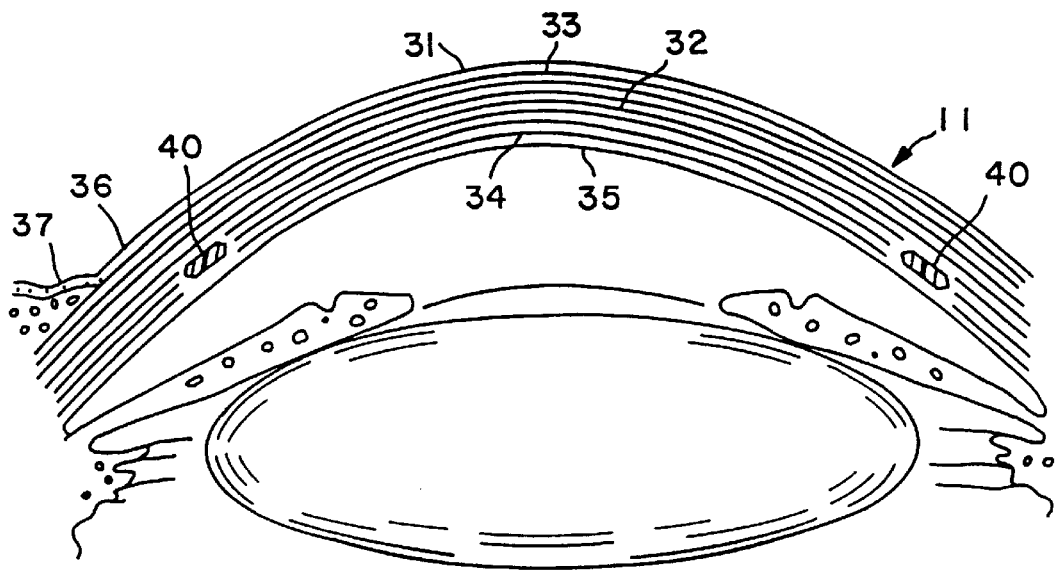
FIG. 2 is a schematic illustration of the anterior portion of the eye showing the various layers of the cornea.

FIG. 2 is a more detailed drawing of the anterior portion of the globe showing the various layers of the cornea (11) making up the epithelium (31) and the general placement of the ICR (40). Epithelial cells on the surface thereof function to maintain transparency of the cornea (11). These epithelial cells are rich in glycogen, enzymes and acetylcholine and their activity regulates the corneal corpuscles and controls the transport of water and electrolytes through the lamellae of the stroma (32) of the cornea (11).

An anterior limiting lamella (33), referred to as Bowman's membrane or layer, is positioned between the epithelium (31) and the stroma (32) of the cornea. The stroma (32) is made up of lamellae having bands of fibrils parallel to each other and crossing the whole of the cornea. While most of the fibrous bands are parallel to the surface, some are oblique, especially anteriorly. A posterior limiting lamina (34) is referred to as Descemet's membrane. It is a strong membrane sharply defined from the stroma (32) and resistant to pathological processes of the cornea.

The endothelium (35) is the most posterior layer of the cornea and consists of a single layer of cells. The limbus (37) is the transition zone between the conjunctiva and sclera on the one hand and the cornea(11) on the other.

Figure 3:
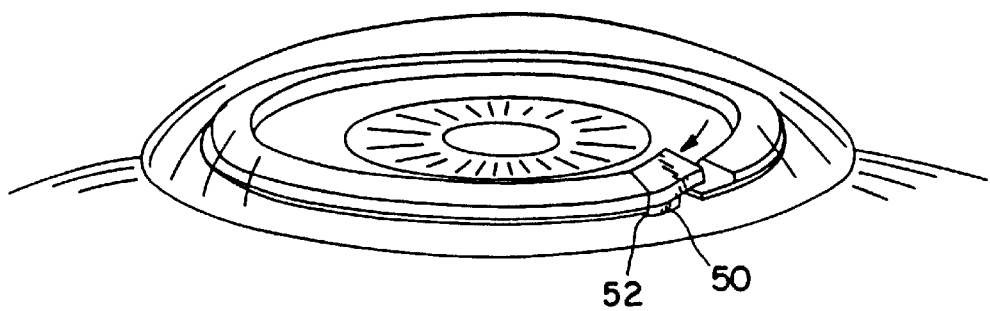
FIG. 3 shows the step of inserting the inventive intrastromal corneal ring through an incision in the cornea.

FIG. 3 shows the completion of the step of inserting the hybrid intrastromal corneal ring into the corneal stroma. Techniques such as that shown in our copending application Ser. No. 07/867,745, entitled CORNEAL VACUUM CENTERING GUIDE AND DISSECTOR, filed Apr. 10, 1992, are suitable for preparing the eye and inserting the intrastromal corneal ring into the appropriately prepared interlamellar stromal channel. Generally the ICR (50) is installed in the following manner: A small radial incision (52) is made at the corneal radius in which the intrastromal corneal ring is ultimately to be installed about the cornea. A dissector in the form of a split ring having a point suitable for producing the interlamellar channel in the corneal stroma is introduced into the stromal space through the small incision. It is then rotated in such a fashion that a generally circular channel is formed completely encircling the cornea. The dissector is then rotated in the opposite direction to withdraw it from the tunnel or channel thus formed. An intrastromal corneal ring is then introduced into the circular channel and joined at its ends. Hybrid intrastromal corneal ring having partially hydrated polymers on their outer periphery are typically slippery and consequently may be introduced into the interlamellar tunnel with great ease. It is usually desirable to (at least partially) hydrate the hybrid ICR in that, otherwise, the ICR during its traverse through the tunnel may desiccate the path and begin to stick to the interior wall of the tunnel. The ICR may be lubricated with suitable ocular lubricants such as hyaluronic acid, methylethyl cellulose, dextran solutions, glycerine solutions, polysaccharides, or oligosaccharides upon its introduction to help with the insertion particularly if one wishes to insert the hybrid intrastromal corneal ring without any hydration.

Figure 4:
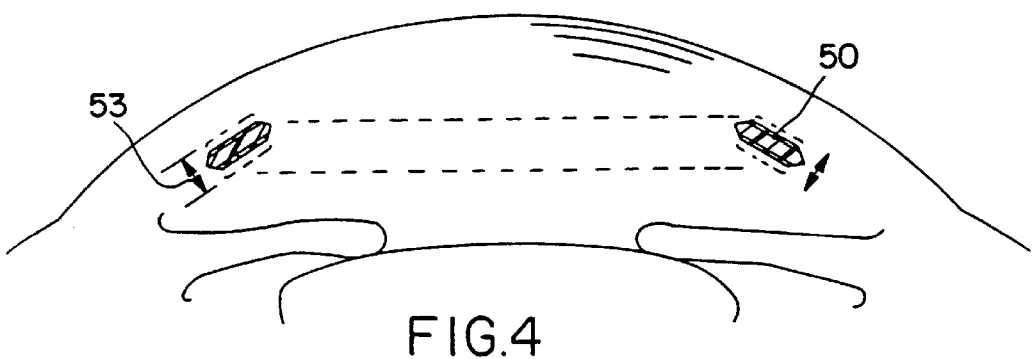
FIG. 4 shows, in partial cross-section, the anterior portion of an eye with the hybrid intrastromal corneal ring installed.

FIG. 4 shows, in cross-section, the anterior portion of the eye with the hybrid intrastromal corneal ring (50) inserted. Subsequent to the insertion, the intrastromal corneal ring (50) will swell to its final size or thickness (53) within the eye. This swelling permits the inclusion of larger intrastromal corneal ring than would normally be accommodated within normal sized intrastromal channels.

Figure 5A:
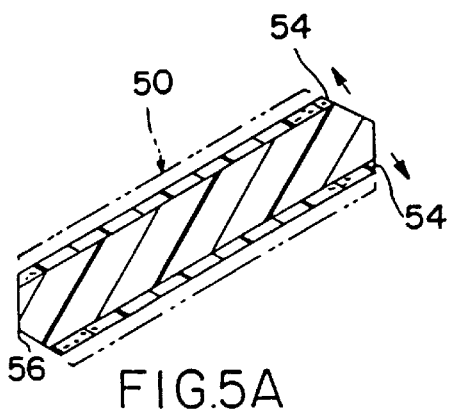
FIGS. 5A and 5B show, in cross-section, respectively, an unhydrated and a hydrated ring in which the hydratable, low modulus polymer is placed on only two surfaces.

FIG. 5A shows in cross-section the hybrid intrastromal corneal ring having inner and outer faces (54) comprising polymers having low moduli of elasticity. Low modulus polymers are those having a modulus of elasticity below about 3.5 kpsi, more preferably between 1 psi and 1 kpsi, and most preferably between 1 psi and 500 psi. They must be physiologically compatible with the eye. Most polymeric materials used in soft contact lenses are suitable for the outer layer contemplated in this invention. In addition, the class includes physiologically compatible elastomers such a polyacrylates, silicones, isoprene, and the like. Additionally, low modulus polymers include biologic polymers such as crosslinked dextran, crosslinked heparin or hyaluronic acid.

The inner portion or core (56) as shown in FIG. 5A is a physiologically compatible polymer having a high modulus of elasticity. A high modulus of elasticity is considered to be greater in value than about 3.5 kpsi, preferably 5–12 kpsi, and most preferably 8–10 kpsi. These polymers are typically stiffer and may be materials such as polymethyl methacrylate (PMMA), TEFLON (PTFE), longer chain silicone polymers such as are used in hard contact lenses. Additionally, suitable polymers include polycarbonates; polyolefins such as polyethylene, polypropylene, and polybutylene, their mixtures and polyolefin interpolymers, block copolymers and the like.

The extent to which the outer layers swell upon hydration is dependent upon the type of polymer chosen and, when the polymer is hydratable, upon the amount of cross-linking found in the outer layers (54), and on the thickness of the layer. Generally speaking, the more highly linked the hydratable polymer, the smaller the amount of volume change upon hydration. Conversely, a polymer having only sufficient cross-linking for strength in the service in which this device is placed, will have a somewhat lower level of cross-linking. Alternatively, a substantially nonswellable polymer system may be formed of a hydrogel physically interpenetrated by another polymer which does not hydrate, e.g., polyHEMA with polyacylnitrite.

The thickness of the outer layer depends in large function upon the intended use of the ICR. For instance if the outer layer is to be used as a container for an inner volume of a settable polymer or drug, the outer layer may be relatively thicker. If the outer layer is used to provide a swellable outer layer which does not add significantly to the size of the ICR or is used functionally as a lubricant layer, the other layer may be quite thin even to the point of a layer of minimum coverage, perhaps as thin as a molecule thick.

Figure 5B:
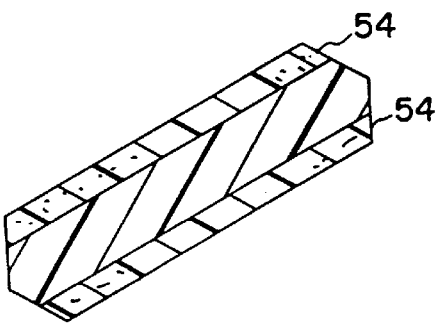

FIG. 5B shows the hybrid ICR of FIG. 5A after it has been completely hydrated and the polymer faces (54) have swollen to their largest extent.

The inventive device shown in FIGS. 5A and 5B may also be used in the instance where a low modulus covering is not placed over the entire outside surface of the intrastromal corneal ring. For instance, to alleviate astigmatism, an ICR having a thick portion and a thin portion may be desired. An ICR having an inner core of a high modulus polymer and an outer covering of a swellable polymer might be chosen. The surgeon would remove a portion of the intrastromal corneal ring exterior coating or face prior to introducing the ICR into the eye. Such an intrastromal corneal ring and its use are described more fully in Ser. No. 07/939,492, entitled ASTIGMATIC CORRECTING INTRASTROMAL CORNEAL RING, filed Sep. 3, 1992.

Figure 6:
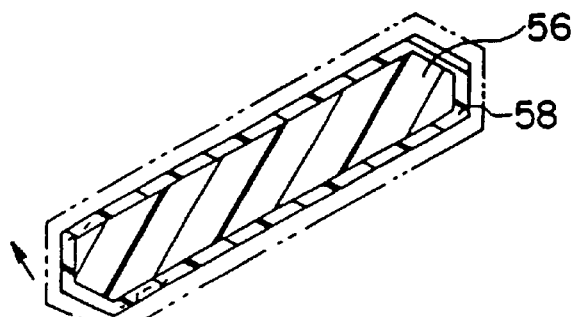
FIG. 6 shows in cross-section an unhydrated hybrid ICR in which the hydratable, low modulus polymer completely coats the ring.

FIG. 6 shows a hybrid intrastromal corneal ring in which the core (56) is of high modulus polymeric material such as mentioned above. In this variation the outer surface is completely coated with a swellable polymer or polymeric gel such as those discussed above. Again, the composition of outer covering (58) may be of a hydratable polymer system which is sufficiently cross-linked that the polymer does not swell appreciably upon hydration. Alternatively, the covering (56) may be cross-linked only so much as to allow substantial swelling of the outer covering either before or after insertion into the eye.

Figure 7:
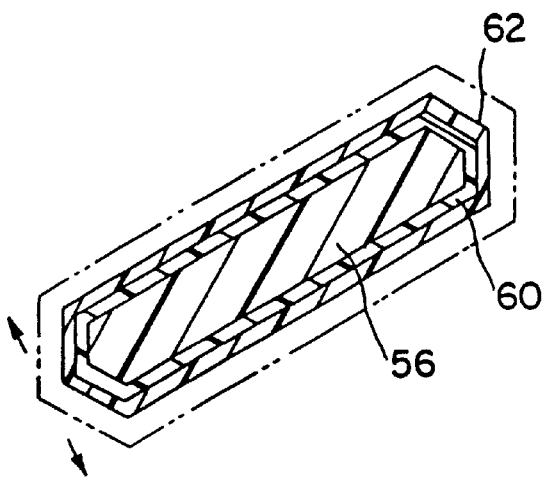
FIG. 7 shows a multiply-coated intrastromal corneal ring.

FIG. 7 shows another variation of the inventive hybrid intrastromal corneal ring. In this variant of the inventive hybrid intrastromal corneal ring, the inner high modulus core (56) is surrounded by more than one layer, specifically, an intermediate layer (60) and an outer layer (62). This hybrid intrastromal corneal ring may be appropriate when the outer layer (62) is difficult to bond to the core (56). An intermediate layer (60) which bonds both to the core (56) and to the outer layer (62) may be used. Intermediate layer (60) typically would not be a polymer which swells appreciably upon hydration lest it split outer layer (62). Outer layer (62) may either swell upon hydration, as is shown in FIG. 7, or may remain at approximately the same size upon hydration if a suitably low modulus polymer system is chosen.

Figure 8:
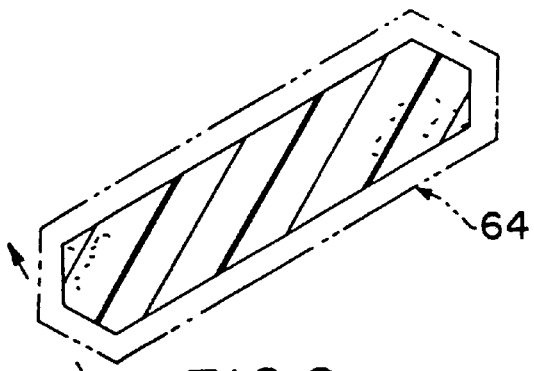
FIG. 8 shows, in cross-section, an intrastromal corneal ring comprising a swellable, low modulus polymer.

FIG. 8 shows an intrastromal corneal rings made of a low modulus, hydratable polymer such as those discussed above. Since these polymers often lose substantial mechanical strength upon hydration, these ICRs would be inserted into the intrastromal space prior to being hydrated or with the assistance of a tool either before or after hydration.

Figure 9A:
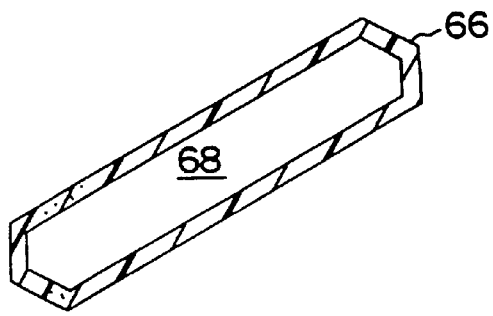
FIGS. 9A and 9B show, in cross-section, an ICR comprising a fillable shell which is nonhydrated in FIG. 9A and hydrated and swollen in FIG. 9B. The FIG. 9B intrastromal corneal ring contains a fluid.

FIG. 9A shows an intrastromal corneal ring made of a low modulus polymer system hydratable outer coating (66) and an inner cavity (68). This intrastromal corneal ring may be inserted into the intrastromal space created by the dissector (as described above) as a covering on a tool similar to the dissector which created the intracorneal channel. Once in position the insertion tool is rotated out of the intrastromal corneal ring leaving the shell within the stroma.

Alternatively, the intrastromal corneal ring may be introduced into the intrastromal channel as the dissector is fully rotated in place, attached to the leading edge of the dissector, and pulled into the intrastromal channel as the dissector is rotated out of the eye.

Figure 9B:
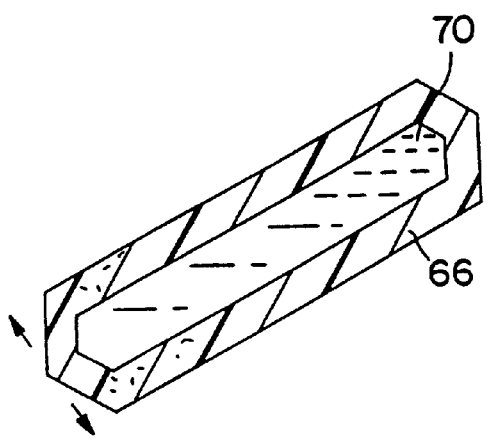

FIG. 9B shows the intrastromal corneal ring of FIG. 9A upon completion of the hydration in that the outer covering (66) is swollen to its largest extent. Furthermore, the inner cavity (68) (FIG. 9A) may be filled with a biologic, drug or other liquid, or biologically active eye treatment material (7a). These devices may be tied or otherwise connected at their point of insertion by known techniques.

The shell may be injected with a settable soft polymer core and allowed to expand to a desired thickness. Suitable injectable polymers are well known but include polyHEMA hydrogel, cross-linked collagen, cross-linked hyaluronic acid, siloxane gels, and organic-siloxane gels such as cross-linked methyl vinyl siloxane gels. The injected polymer sets after injection.

Figure 10A:
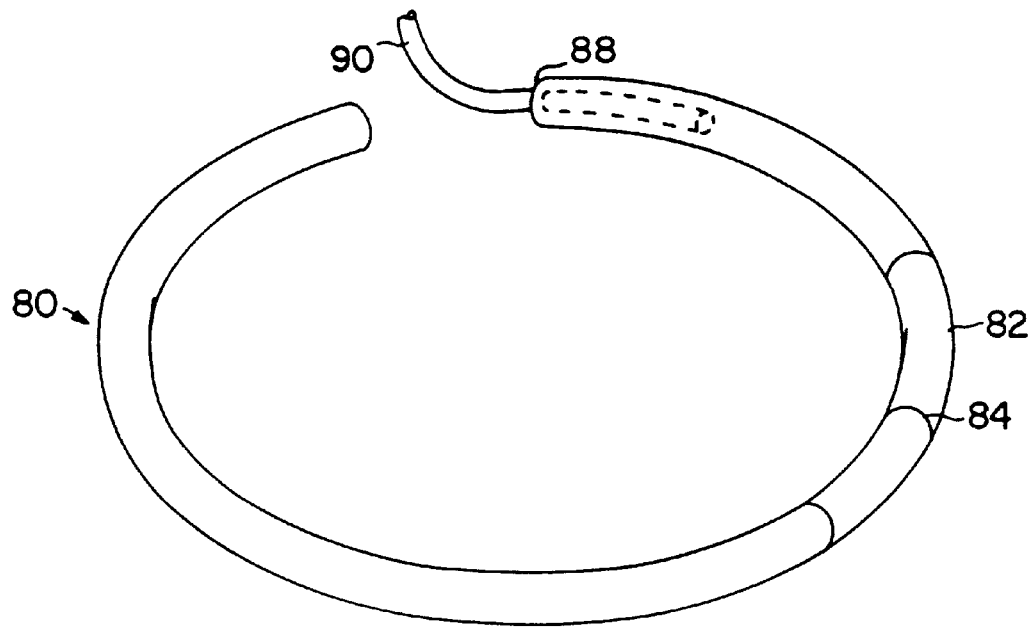
FIGS. 10A and 10B show a baffled soft intrastromal corneal ring.
Figure 10B:
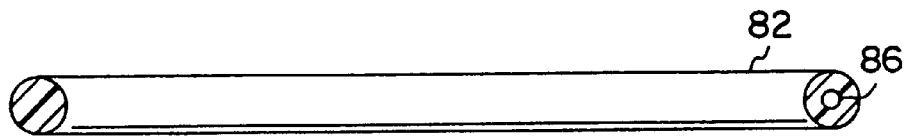

FIGS. 10A and 10B show a variation of the inventive intrastromal corneal ring (80) in which a polymeric ring containing a number of chambers (82) separated by baffle walls (84) which may have an optional hole (86) in the baffle wall (84). Once the intrastromal corneal ring is introduced into the eye, it may be filled with a drug or biologic material via injection with a suitable syringe through the intrastromal corneal ring wall or into the end (88) of the tube. A settable polymer of the type discussed above may be introduced into the chambers in similar fashion if a ring of variable bulk is required. It is also appropriate to include a smaller fill tube (90) which extends through the end (88) of the tube (80) through the holes (86) in the baffle walls (84). In this way drugs, biologic agents, or settable polymers may be delivered in a specific fashion throughout the ring as the fill tube is withdrawn from the intrastromal corneal ring.

Figure 11:
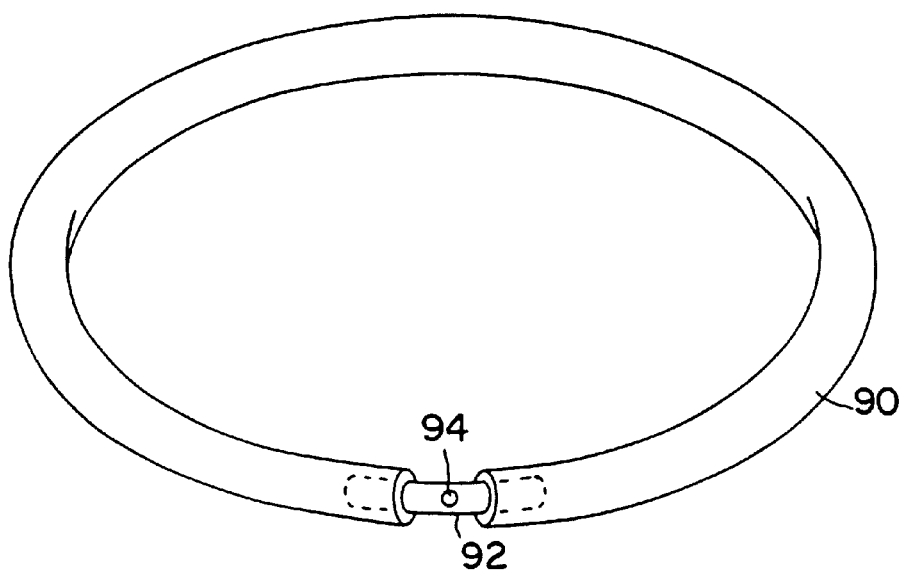
FIG. 11 shows an end-to-end intrastromal corneal ring connector which permits introduction of drugs or a settable polymer.

FIG. 11 shows a connector (92) situated between the ends of an intrastromal corneal ring (96). The intrastromal corneal ring is a low modulus polymer having a hollow center. The connector has a receiver port (94) suitable for introducing drugs, biologics, or settable polymers into the interior of the intrastromal corneal ring. The connector has a passageway connecting the receiver port (94) into the intrastromal corneal ring interior.

In the variation of the invention specified just above and shown in FIGS. 10A, 10B, and 11, the wall or outer covering of the intrastromal corneal ring may be a hydratable low modulus polymer or an elastomer. If an elastomeric polymer is selected, the intrastromal corneal ring may be injected with a settable polymer as specified.

The low modulus polymers used in this invention are often absorbent, particularly if they are hydratable, and may be infused with a drug or biologic agent which may be slowly released from the device after implantation of the intrastromal corneal ring. For instance, the low modulus polymer may be loaded with a drug such as dexamethasone to reduce acute inflammatory response to implanting the device. This drug helps to prevent undesirable scarring or vascular ingrowth toward the intrastromal corneal ring. Similarly, heparin, corticosteroids, antimitotics, antiinflammatories, and antiangiogenesis factors (such as nicotine adenine dinucleotide ($NAD^+$)) may be included to reduce or prevent angiogenesis and inflammation.

Clearly, there are a variety of other drugs suitable for inclusion in the intrastromal corneal ring. The choice will depend upon the use to which the drugs are put.

The terms and expressions which have been used in the description above are used only as terms of description and not of limitation. There is no intention of excluding equivalents of the features shown or described. It is recognized that one having ordinary skill in this art would perceive equivalence to the inventions claimed below, which equivalence would be within the spirit of the invention as expressed above.

I claim as my invention:

1. An intracorneal ring adapted for implantation within a human cornea and configured to alter the curvature of the cornea to effect refractive correction of an eye, said ring comprising at least one inner layer comprising a high elastic modulus, physiologically compatible polymer and at least one outer layer comprising a low elastic modulus, physiologically compatible polymer.

2. The ring of claim 1 wherein the low elastic modulus physiologically compatible polymer is selected from hydratable polymers which swell upon hydration and hydratable polymers which do not swell upon hydration.

3. The ring of claim 2 wherein the low elastic modulus polymer comprises a polymer selected from polyhydroxyethyl methylacrylate and polyvinylpyrrolidone.

4. The ring of claim 1 wherein the low elastic modulus, physiologically compatible polymer comprises an elastomer.

5. The ring of claim 1 wherein said high elastic modulus polymer comprises at least one polymer selected from PMMA, poly(tetrafluoroethylene), silicone, polycarbonate, a polyolefin selected from polyethylene, polypropylene, polybutylene, and mixtures or interpolymers thereof.

6. The ring of claim 1 wherein the low elastic modulus polymer comprises at least one polymer selected from latex rubber, polysilicones, polyurethanes, polyesters, and polyacrylates.

7. The ring of claim 1 wherein said ring comprises a third layer between the outer layer and the inner layer having an adhesion to the inner layer and to the outer layer that is greater than the adhesion of the inner layer to the outer layer.

8. The ring of claim 1 wherein said ring is a split ring.

9. An intracorneal ring adapted for implantation within a human cornea and configured to alter the curvature of the cornea to effect refractive correction of an eye, said ring comprising a physiologically compatible polymeric inner portion and a physiologically compatible polymeric outer portion, said outer portion having a low elastic modulus and said inner portion having an elastic modulus that is greater than the elastic modulus of the outer portion.

10. The ring of claim 9 wherein the inner portion has a high elastic modulus.

11. The ring of claim 9 wherein the ring is a split ring.

12. An intracorneal implant shaped to be inserted in an intracorneal channel in a circumferential direction about the optic axis of a human eye and configured to alter the curvature of the cornea to effect refractive correction of an eye, said implant comprising an elongated arcuate member having ends and having a polymeric outer portion having a first elastic modulus and a polymeric inner portion having a second elastic modulus, wherein the first elastic modulus differs substantially from the second elastic modulus.

13. The implant of claim 12 wherein the polymeric outer portion has a low elastic modulus.

14. The implant of claim 13 wherein the polymeric outer portion comprises at least one polymer selected from hydratable polymers which swell upon hydration and hydratable polymers which do not swell upon hydration.

15. The implant of claim 13 wherein the polymeric outer portion comprises an elastomer.

16. The implant of claim 13 wherein the outer portion comprises at least one polymer selected from latex rubber, polysilicones, polyurethanes, polyesters, and polyacrylates.

17. The implant of claim 13 wherein the polymeric inner portion has a high elastic modulus.

18. The implant of claim 12 wherein the polymeric inner portion has a high elastic modulus.

19. The implant of claim 18 wherein the inner portion comprises at least one polymer selected from PMMA, poly(tetrafluoroethylene), silicone, polycarbonate, a polyolefin selected from polyethylene, polypropylene, polybutylene, and mixtures or interpolymers thereof.

20. An intracorneal implant shaped to be inserted in an intracorneal channel in a circumferential direction about the optic axis of a human eye and configured to alter the curvature of the cornea to effect refractive correction of an eye, said implant comprising an elongated arcuate member having an outer surface and having ends, wherein the outer surface has a first polymeric portion having a first elastic modulus and a second polymeric portion having a second elastic modulus, and wherein the first elastic modulus differs substantially from the second elastic modulus.

21. The implant of claim 20 wherein the first polymeric portion has a low elastic modulus.

22. The implant of claim 21 wherein the first polymeric portion comprises at least one polymer selected from latex rubber, polysilicones, polyurethanes, polyesters, and polyacrylates.

23. The implant of claim 21 wherein the second polymeric portion has a high elastic modulus.

24. The implant of claim 23 wherein the second polymeric portion comprises at least one polymer selected from PMMA, poly(tetrafluoroethylene), silicone, polycarbonate, a polyolefin selected from polyethylene, polypropylene, polybutylene, and mixtures or interpolymers thereof.

25. An intrastromal implant shaped to be inserted in an intracorneal channel in a circumferential direction about the optic axis of a human eye and configured to alter the shape of the cornea by substantially a predetermined amount to effect a desired refractive correction of an eye, said implant comprising an elongated arcuate member having ends which comprises an inner physiologically-compatible polymeric portion having a high elastic modulus and an outer physiologically-compatible polymeric portion having a low elastic modulus.

26. The implant of claim 25 wherein the inner portion comprises a single polymeric layer.

27. The implant of claim 26 wherein the outer portion comprises a single polymeric layer.

28. An intracorneal implant shaped to be inserted in an intracorneal channel in a circumferential direction about the optic axis of a human eye and configured to alter the curvature of the cornea to effect refractive correction of an eye, said implant comprising an elongated arcuate member that comprises a physiologically compatible polymeric inner portion having a first elastic modulus and a physiologically compatible polymeric outer portion having a second elastic modulus, said outer portion being hydratable and said first elastic modulus differing substantially from said second elastic modulus.

29. The implant of claim 28 wherein the outer portion has a low elastic modulus.

30. The implant of claim 29 wherein the inner portion has a high elastic modulus.

31. The implant of claim 28 wherein the implant comprises a split ring.

32. The implant of claim 28 wherein the outer portion comprises an outer layer comprised of a low elastic modulus polymer.

33. The implant of claim 32 wherein the inner portion comprises an inner layer comprised of a high elastic modulus polymer.

* * * * *